United States Patent
Bublewitz et al.

(10) Patent No.: US 6,352,177 B1
(45) Date of Patent: Mar. 5, 2002

(54) DEVICE FOR DISCHARGING A PASTY TWO-COMPONENT MIXTURE

(75) Inventors: Alexander Bublewitz, Herborn; Matthias Suchan, Hachenburg, both of (DE)

(73) Assignee: Kettenbach GmbH & Co. KG, Eschenburg (DE)

( * ) Notice: Subject to any disclaimer, the term of this patent is extended or adjusted under 35 U.S.C. 154(b) by 0 days.

(21) Appl. No.: 09/807,516
(22) PCT Filed: Oct. 14, 1999
(86) PCT No.: PCT/EP99/07704
§ 371 Date: Apr. 16, 2001
§ 102(e) Date: Apr. 16, 2001
(87) PCT Pub. No.: WO00/21653
PCT Pub. Date: Apr. 20, 2000

(30) Foreign Application Priority Data

Oct. 14, 1998 (DE) .................................... 298 18 280 U

(51) Int. Cl.⁷ .................................................. B67D 5/00
(52) U.S. Cl. ........................................ 222/82; 222/137
(58) Field of Search ........................... 222/137, 145.6, 222/569, 570, 83, 82

(56) References Cited

U.S. PATENT DOCUMENTS 5,242,082 A * 9/1993 Giannuzi .................... 222/82
5,875,928 A * 3/1999 Muller et al. ............... 222/137

FOREIGN PATENT DOCUMENTS

EP 0 730 913 A1 9/1996
EP 0 787 655 A1 8/1997

* cited by examiner

Primary Examiner—Philippe Derakshani
(74) Attorney, Agent, or Firm—Diller, Ramik & Wight

(57) ABSTRACT

A device for the discharge of a pasty two-component mixture includes a supply container with two chambers, each chamber for containing one component of the two-component mixture and having an outlet stub for connecting to a mixer unit. The mixer unit includes a coupling end having two inlet stubs which form two channels leading into a mixer element, and on an opposite end, an outlet opening. A rotatable holding shell is provided in a substantially surrounding relationship to the two outlet stubs and includes a recess of a shape substantially identical with the cross sectional shape of the coupling end of the mixer housing.

59 Claims, 7 Drawing Sheets

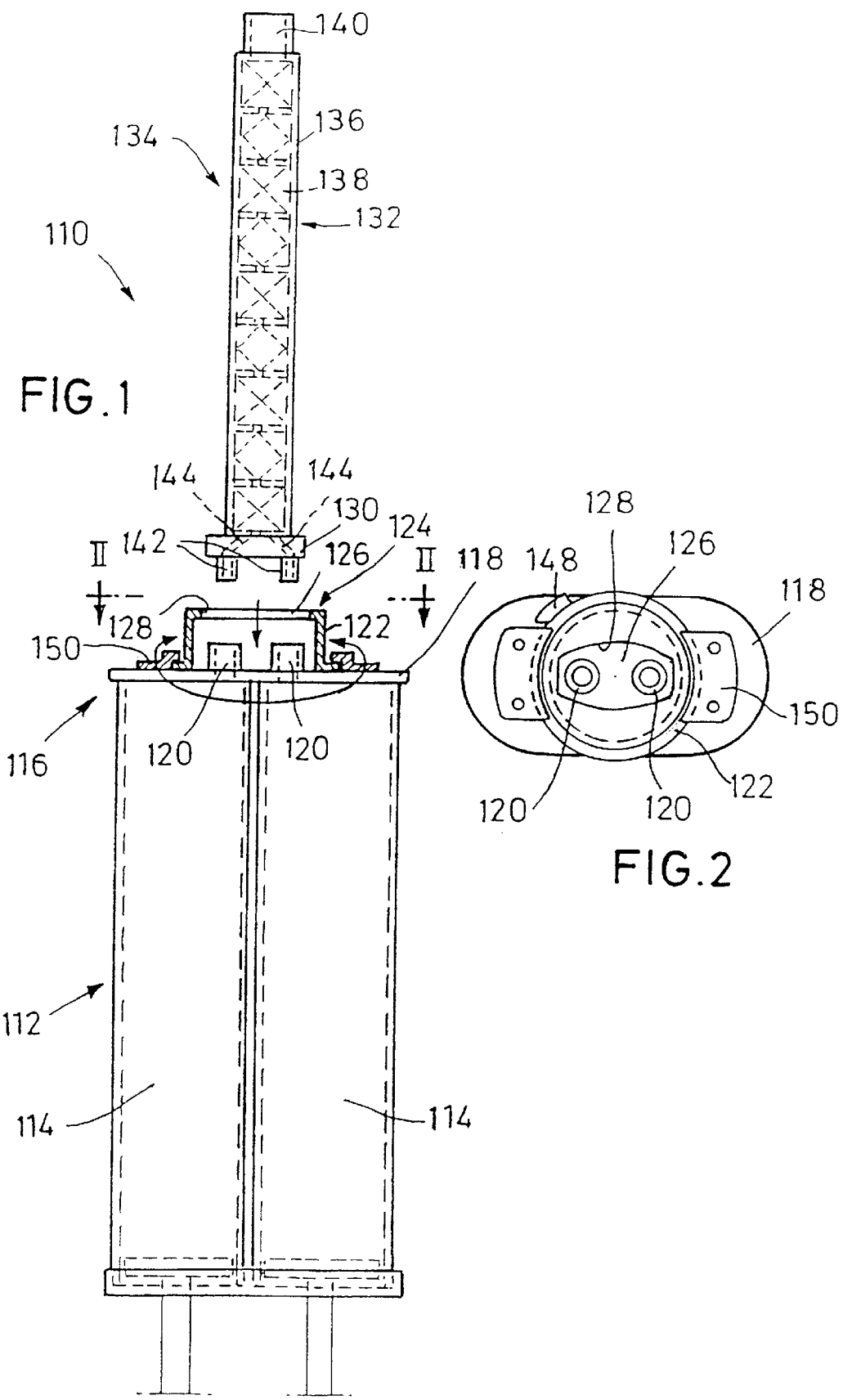

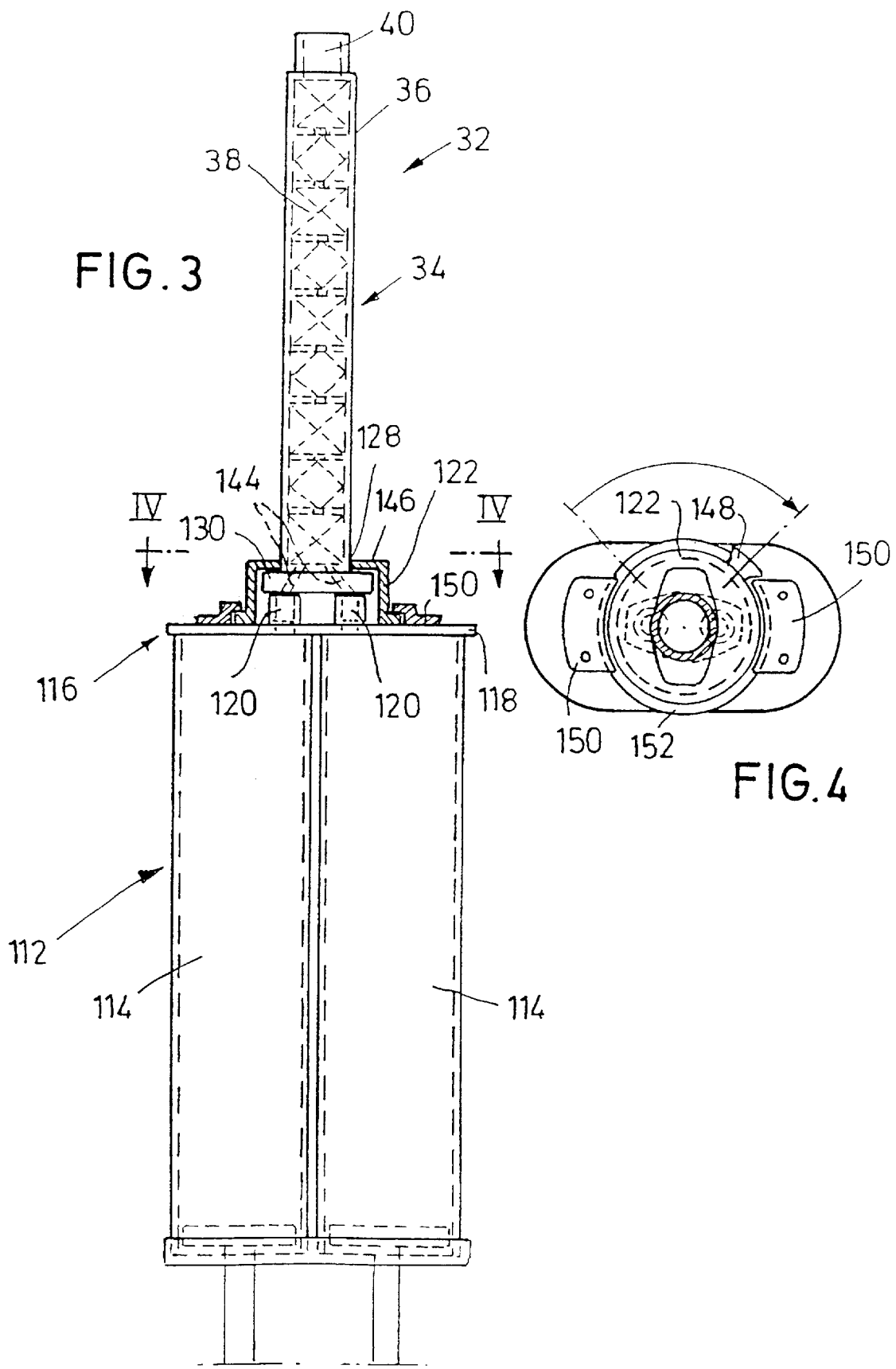

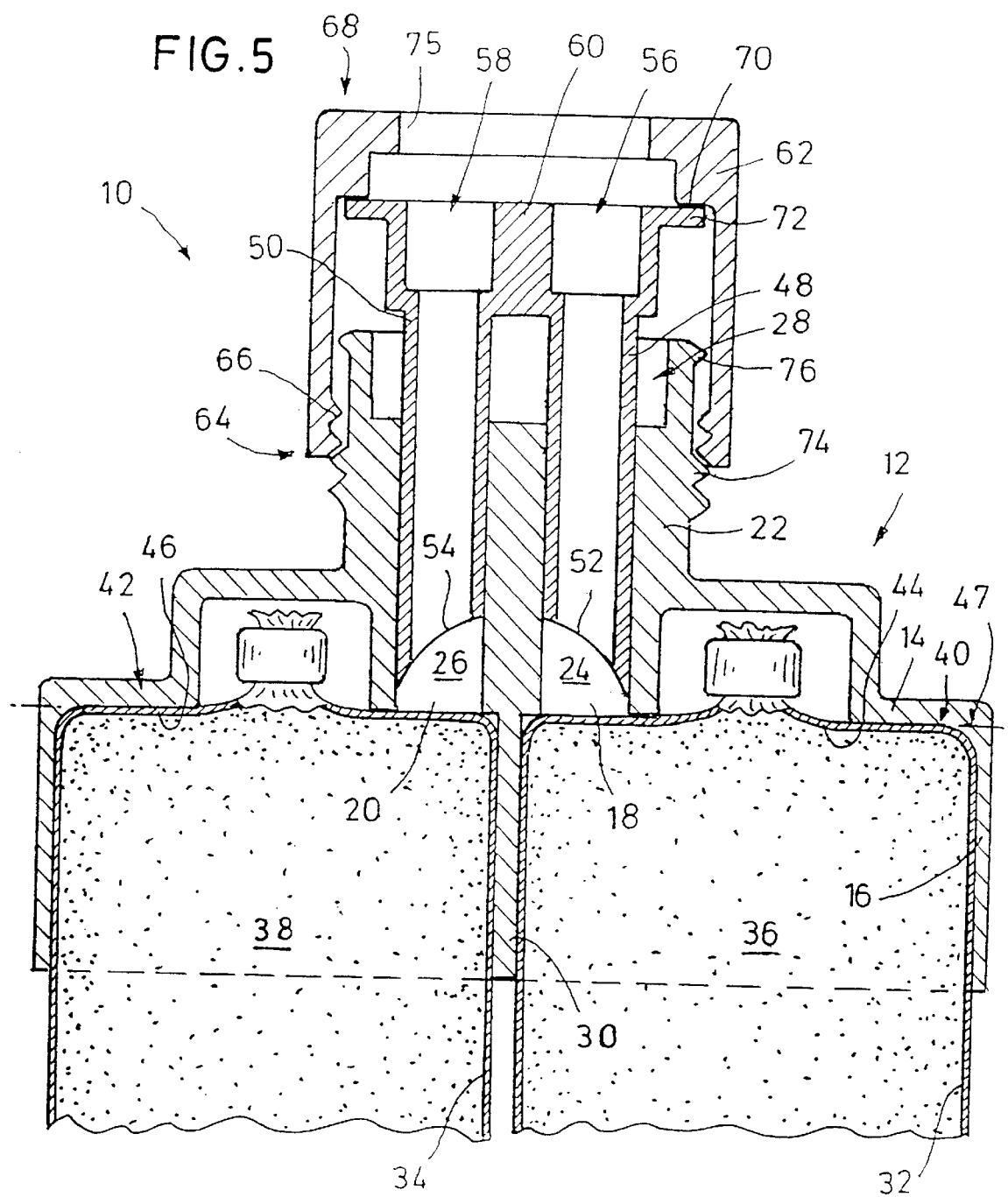

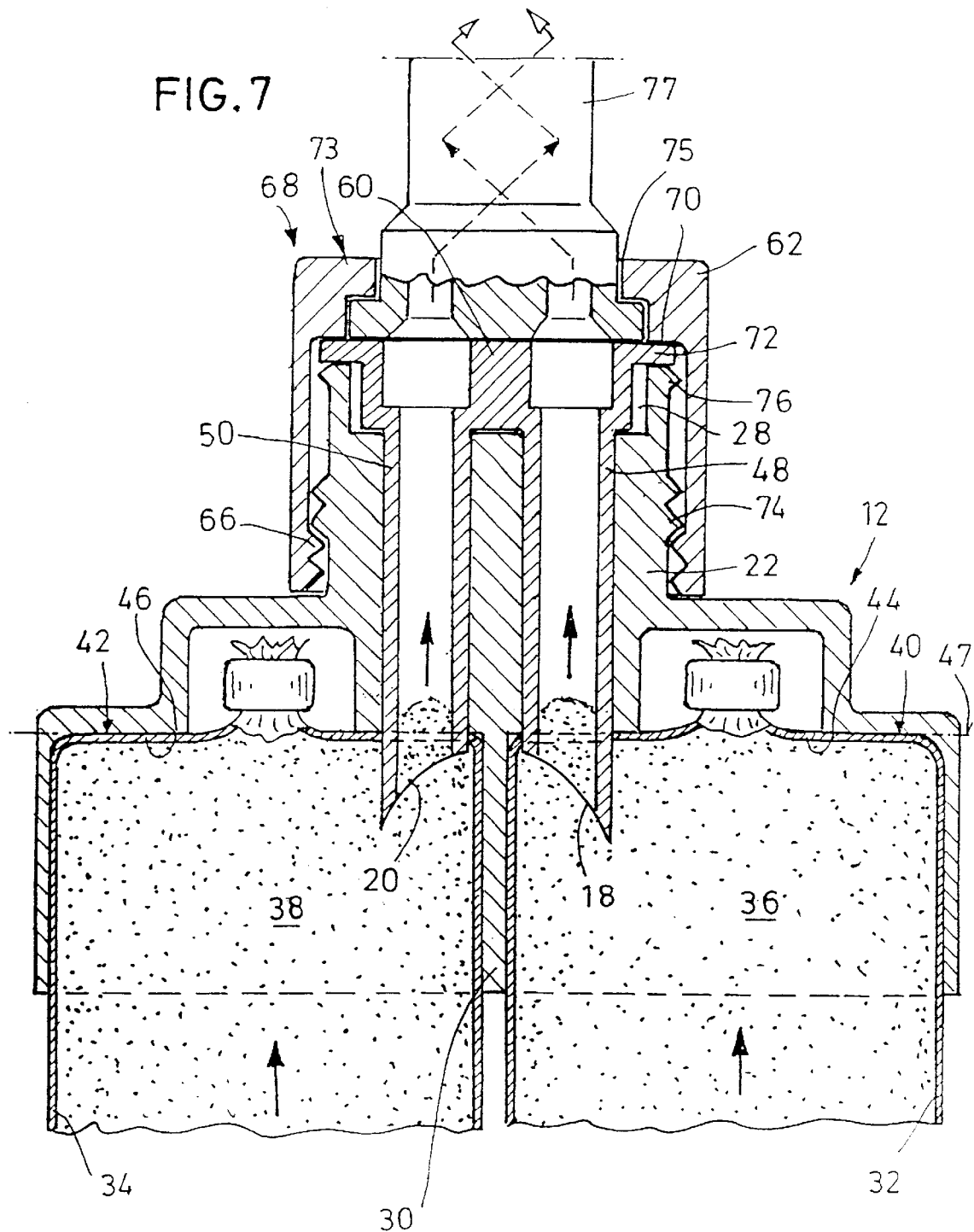

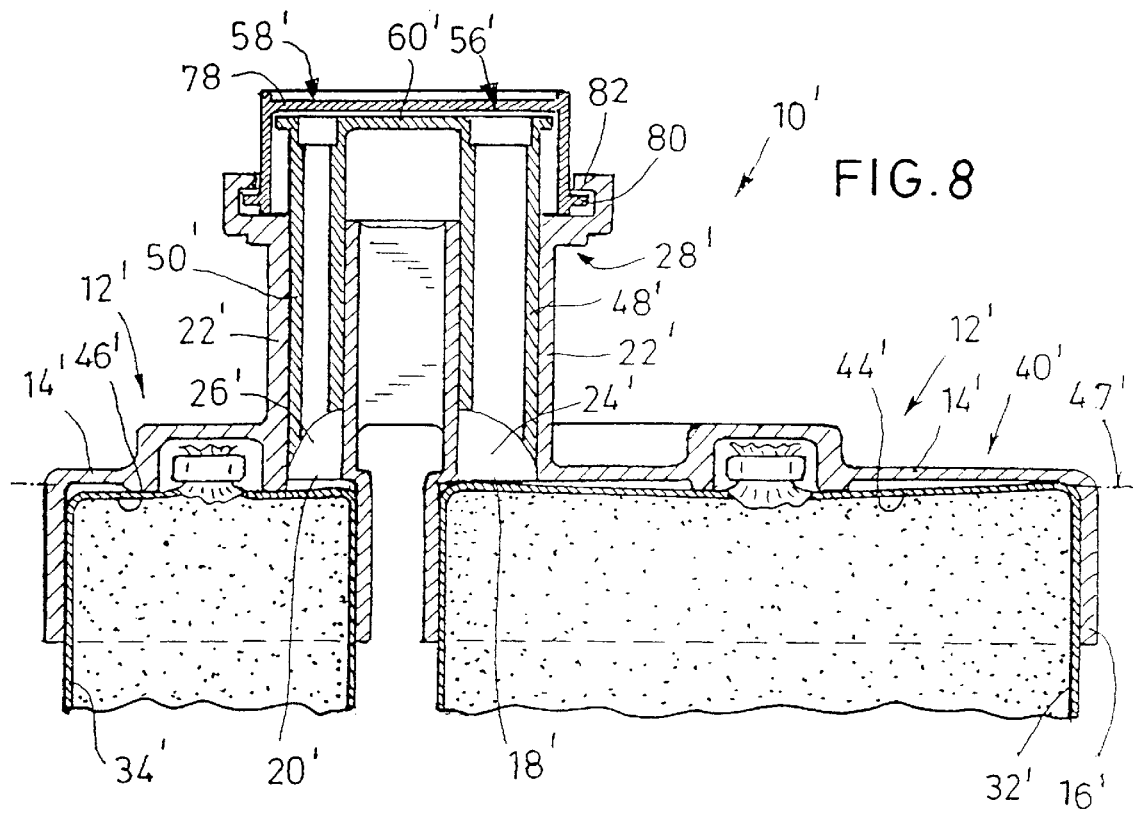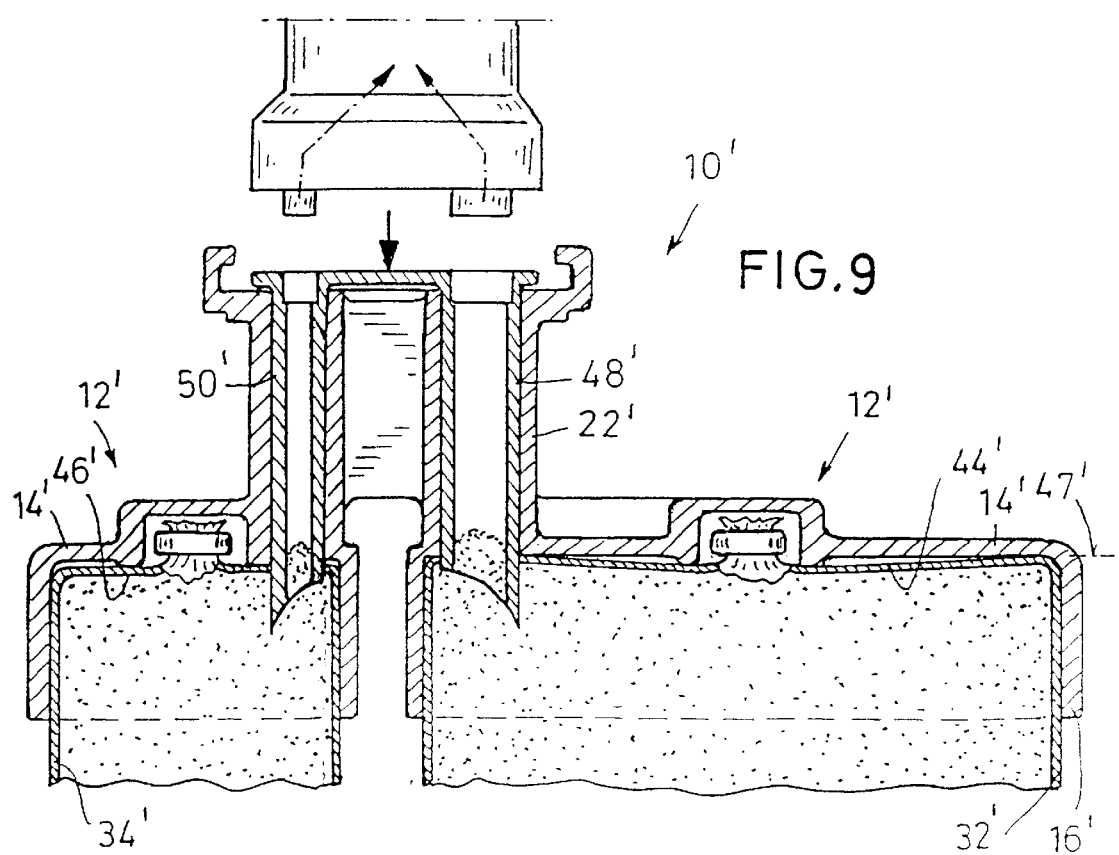

DEVICE FOR DISCHARGING A PASTY TWO-COMPONENT MIXTURE

BACKGROUND OF THE INVENTION

The invention relates to a device for discharging a pasty two-component mixture, e.g. a mixture of a dental impression substance and a catalyst for initiating or accelerating the hardening.

SUMMARY OF THE INVENTION

For applying multi-component substances in mixed form, discharge devices are known which comprise a supply container with at least two chambers for respectively one of the pasty components of the mixture. Assigned to each chamber is an outlet stub for discharging the pasty substance upon application of pressure. To allow discharge of the pasty substances in mixed form, the outlet stubs of the known devices have a mixer unit mounted thereon, comprising a mixer housing including a substantially tubular portion and a coupling end for attachment to a supply container. In the tubular portion of the mixer housing, a mixer element is arranged by which the components, which have been supplied via separate channels, are subjected to a turbulence and mixing effect. Said channels are formed in the coupling end of the mixer housing and extend from the inlet stub of the coupling end to the mixer element. A device of this type is known e.g. from EP-A-0 730 913.

Depending on the composition of the pasty components, their mixing will result in the respectively desired chemical reactions. For instance, if one of the two pasty components is a dental impression substance, the adding of a second component initiates and accelerates the polymerisation of this impression substance. Should this second component (also referred to as a catalyst) penetrate, via the mixer unit, from the one chamber into the other chamber of the supply container or should already the outlet stub of the chamber for the dental impression substance by contaminated with the catalyst, the whole device will be rendered useless, which, depending on the extent to which the chambers are filled, will cause a considerable loss of expensive material. Therefore, the two component flows have to remain separated from each other for the longest possible stretch of their moving paths and be brought together only within the tubular portion of the mixer housing.

In the known discharge device for pasty two-component mixtures, the mixer housing is detachably locked to the supply container by means of a holding shell. The holding shell is supported for rotation on the mixer housing and is provided with radially outward locking projections formed in the manner of bayonet locks, which can be rotated to move under corresponding grip-over projections of the supply container.

The invention further relates to a device for opening a tube bag containing a pasty substance. Said device is further provided to guide the pasty substance out of the tube bag.

The pasty substances are offered in rigid containers or cartridges with displaceable bottom walls which are advanced by plunger elements arranged to be advanced by hand or by means of an engine in order to exert pressure on the pasty substances, thus discharging the substances from the cartridges and the cartridges or containers. In recent years, for reducing the packing material, the pasty substances have been increasingly offered in tube bags. For discharging the pasty substances, the tube bags have to be opened, preferably on their end sides. This is preferably performed by means of stationary piercing mandrels or the like cutting elements arranged on the end wall of a holding cap surrounding the end side of the tube bag and comprising a discharge stub. From EP-A-0 787 655, it is known to provide the inner projection of the holding cap with a piercing tube resiliently biased in the direction of the end face of the end of the tube bag. The as of yet known systems for automatic opening of tube bags are in need of improvement in so far as, for opening the tube bag, it is always required to exert pressure onto the tube bag and thus also on the pasty substance in the tube bag. Thus, the process of opening the tube bag is accompanied by the discharge of the pasty substance.

As already mentioned above, discharge devices are used intermittently, the period between two successive uses being possibly so long that the mixture in the mixer unit will harden. As a result, the mixer unit has to be removed and replaced by a new one before the discharge of a mixed substance can be continued. Thus, the mixer unit is a disposable component, making it desirable to keep the number of components of this disposable mixer unit as low as possible.

It is an object of the invention to provide a device for the discharge of a pasty two-component mixture, comprising a mixer unit with a reduced number of parts.

According to the invention, to achieve the above object, there is proposed a device for the discharge of a pasty two-component mixture comprising:

a supply container with two chambers for respectively one pasty component of the mixture, the supply container being provided with a respective outlet stub for each chamber, a mixer unit comprising a tubular mixer housing with a mixer element arranged therein, the mixer housing comprising a coupling end to be coupled to the supply container and having a two inlet stubs and two channels for the pasty components of the mixture leading to the mixer element, and comprising, on its opposite end, an outlet opening for the mixture, the inlet stubs being adapted for insertion into the outlet stubs or vice versa, and a holding shell for the coupling end of the mixer housing arranged for rotation on the supply container, the holding shell surrounding the two outlet stubs and comprising a recess of a shape at least in parts substantially identical with the cross sectional shape of the coupling end of the mixer housing, the holding shell being rotatable between a receiving rotational position in which the recess is oriented corresponding to the orientation of the coupling end of the mixer housing in the state where the inlet stubs are connected to the outlet stubs of the supply container, and a locking rotational position in which at least a part of the recess edge of the holding shell is in engagement over parts of the coupling end of the mixer housing.

In the inventive discharge device, the holding shell holding the mixer unit is arranged not on the mixer housing but on the supply container. On this supply container, the holding shell is supported for rotation about its longitudinal axis. The holding shell surrounds the two outlet stubs of the supply container and is provided, on its front end facing away from the supply container, with a recess which in the first rotational position of the holding shell (receiving rotational position) allows the mixer housing to be mounted onto the outlet stubs of the supply container, while, in a second rotational position (locking rotational position) the edge of the holding shell delimiting the recess has been moved over partial regions of the coupling end, e.g. over radially projecting flange portions of the coupling end of the mixer housing, thus locking the mixer housing to the supply container. Therefore, the holding shell is not a component of the mixer unit anymore and thus will be preserved for the whole period during which the discharge device is used for application of the two-component mixture.

In an advantageous embodiment of the invention, the coupling end is provided with two diametrically opposite and radially extending projections, while the holding shell is formed with a recess of a shape identical with the cross sectional shape of the coupling end at the level of the projections of the latter. Particularly, the coupling end of the mixer housing is of a substantially oval shape in the region of the radial projections. The recess of the holding shell, when in its receiving rotational position, is arranged relative to the outlet stubs of the supply container in the same manner as the inlet stubs of the mixer housing relative to the outer projections. Thus, the coupling end of the mixer housing can be moved through the recess of the holding shell until the inlet stubs of the mixer housing have been received by the outlet stubs of the supply container, or vice versa. In this position, the recess edge of the holding shell is arranged above the outer projections on the coupling end of the mixer housing so that, by rotating the holding shell into the locking rotational position, regions of the recess edge engage the outer projection from above. Suitably, the holding shell is in both of these rotational positions secured against unintended further rotation or reverse rotation, which is preferably accomplished by a corresponding locking effect. For the handling of the holding shell, it is further suitable to allow rotation of the holding shell only between its receiving rotational position and its locking rotational position. In this regard, it would be convenient to realize the limitation of the rotational movement by corresponding stopper elements on the holding shell and the supply container.

For this purpose, the invention proposes a device for opening a tube bag containing a pasty substance, which device does not necessarily have to be realized in combination with the above described mixer holding device although such a combination is preferable, and which comprises a receiving cap for receiving an end side of the tube bag, which end side comprises an end face, the receiving cap comprising an end wall forming an abutment plane for the end face of the tube bag, and an edge extending from the end wall, an opening formed in the end wall and surrounded by a stub projecting from the end wall, and a piercing tube guided in the stub for axial displacement.

In this device, it is provided according to the invention that the piercing tube is manually displaceable from a retracted position in which the piercing tube does not extend beyond the abutment plane into an advanced position in which in the piercing tube extends beyond the abutment plane.

The inventive device is provided with a piercing tube which is guided to be axially displaced in the discharge stub of a receiving cap. In the opened state of the tube bag, the pasty substance will be discharged through this stub to be applied directly, or, in case of a two-component material, to be mixed with another component of the pasty substance. The discharge stub is arranged to radially project from the end wall of the receiving cap, with a continuously surrounding edge projecting from the end wall in a direction opposite to the discharge stub. Thus, the receiving cap surrounds one of the two end sides of the tube bag whose end face abuts the end wall of the receiving cap on an abutment face formed by the latter. The piercing tube of the inventive device is manually displaceable from a retracted position to an advanced position. This displacement can be performed either directly by hand in that the piercing tube is manually shifted within the stub, or indirectly by manually moving an operating element which in turn via an abutment face is in abutment on the piercing tube and thus, when being moved itself, will pull along the piercing tube. In both cases, the piercing tube can be displaced from the retracted position in which it does not protrude beyond the abutment plane of the receiving cap, formed by the end wall, into the advanced position in which is projects beyond the abutment plane and thus, with the receiving cap receiving the tube bag, is immersed into the end face of the latter and opens the tube bag. The piercing tube can be arranged in the stub ex factory and will thus be located in its retracted position. By way of alternative thereto, it can be provided that the piercing tube is inserted into the stub by the user. In both cases, it is suitable if the piercing tube in its retracted position is secured against unintended movement from its retracted position by a locking effect or the like. This is advantageous to the user to whom, under the tactile aspect, the retracted position will be perceivable as a defined position of the piercing tube.

The advantage of the inventive opening device resides in that the process of opening the tube bag is separated from the process of discharging the pasty substance from the tube bag. Thus, the tube bag will not be subjected to an increased pressure when being opened, preventing an undesired escape of pasty substance from the tube bag when the latter is being opened. This facilitates the handling of the tube bags.

The inventive device is useful both for receiving caps for a single tube bags and for combined receiving caps for a plurality of tube bags, e.g. two tube bags. In the latter case, the receiving cap comprises a plurality of discharge stubs respectively provided with one piercing tube. These piercing tubes can be connected to each other to be driven in common into the respective tube bags. Of course, it can also be provided that the piercing tubes are not connected to each other so that each tube bag can be "tapped" separately.

It is particularly convenient if the piercing tube in its retracted position projects beyond the discharge end facing away from the end wall of the receiving cap. Notably, in this case, the axial displacement of the piercing tube can be effected by a mere movement into the stub. Once the piercing tube has been completely moved into the stub, the advanced position has been reached and the piercing tube has been driven into the tube bag.

Suitably, it is provided that the piercing tube in its advanced position is secured against undesired return movement in the direction of the retracted position, and in its retracted position is secured against undesired movements into the advanced position. As already mentioned above, this can be realized by locking the piercing tube in or on the stub. As an alternative thereto, the piercing tube, which in its retracted position projects from the discharge end of the stub, can be protected by a removable protective cap which can be pushed over the stub and fixed to the stub. This protective cap serves for protection during shipment and, prior to insertion of the piercing tube, is removed, e.g. unscrewed, in order to expose the piercing tube. An alternative to the protective cap resides in a spacer arranged between the end of the piercing tube projecting from the stub, and the discharge end of the stub. Particularly, this spacer is formed as a resilient clip surrounding the piercing tube. This resilient clip can be laterally withdrawn from the piercing tube so that the latter can then be axially displaced. The spacer is supported between an outer projection on the piercing tube and the discharge end of the stub.

If the piercing tube is moved not directly manually but indirectly manually via an operating element, this operating element can be utilized as a safety means for protecting the piercing tube from undesired movements from the retracted position into the advanced position. The operating element is suitably provided in the manner of a shell element arranged on the stub and displaceable axially along the stub. This shell element can be locked, in two axial positions corresponding to the retracted position and the advanced position of the piercing tube, to the stub and respectively the receiving cap against undesired axial movements. Advantageously, the shell element is formed as a screw element comprising an inner thread portion adapted for engagement with an outer thread portion on the stub. By means of these threaded portions, the shell element can be axially displaced for driving the piercing tube into the tube bag. Both the shell element and the stub are provided, on both sides of their threaded portions, with regions which are free of threads. As long as the two threaded portions are not in threaded engagement with each other, a rotation of the shell element will not lead to an axial displacement. Besides, the threaded portions, while not in mutual threaded engagement, preclude a linear axial displacement of the shell element. Thus, the latter is secured against undesired axial movements before and after the threaded engagement of the two threaded portions.

Embodiments of the invention will be described in greater detail hereunder with reference to the Figures.

BRIEF DESCRIPTION OF THE DRAWINGS

FIG. 1 is a side view of a discharge device for pasty two-component mixtures (particularly dental impression substances with catalyst), with the mixer unit shown in the state briefly before being coupled to the supply container, FIG. 2 is a plan view of the front end of the supply container to which the mixer unit is fastened, wherein the holding shell, arranged on this end of the supply container, is arranged in its receiving rotational position, FIG. 3 is a lateral view, partially in section, of the discharge device with the mixer unit coupled thereto, FIG. 4 is a sectional view, taken along the line IV—IV of FIG. 3, of the holding shell in its locking rotational position, FIGS. 5 to 7 are views of a further embodiment of a device for the simultaneous opening of two tube bags, with the device shown in different operational states, FIGS. 8 and 9 are views of a third embodiment of an opening device for two tube bags, with the device again shown in different operational states.

DESCRIPTION OF THE PREFERRED EMBODIMENTS

Figure 6:
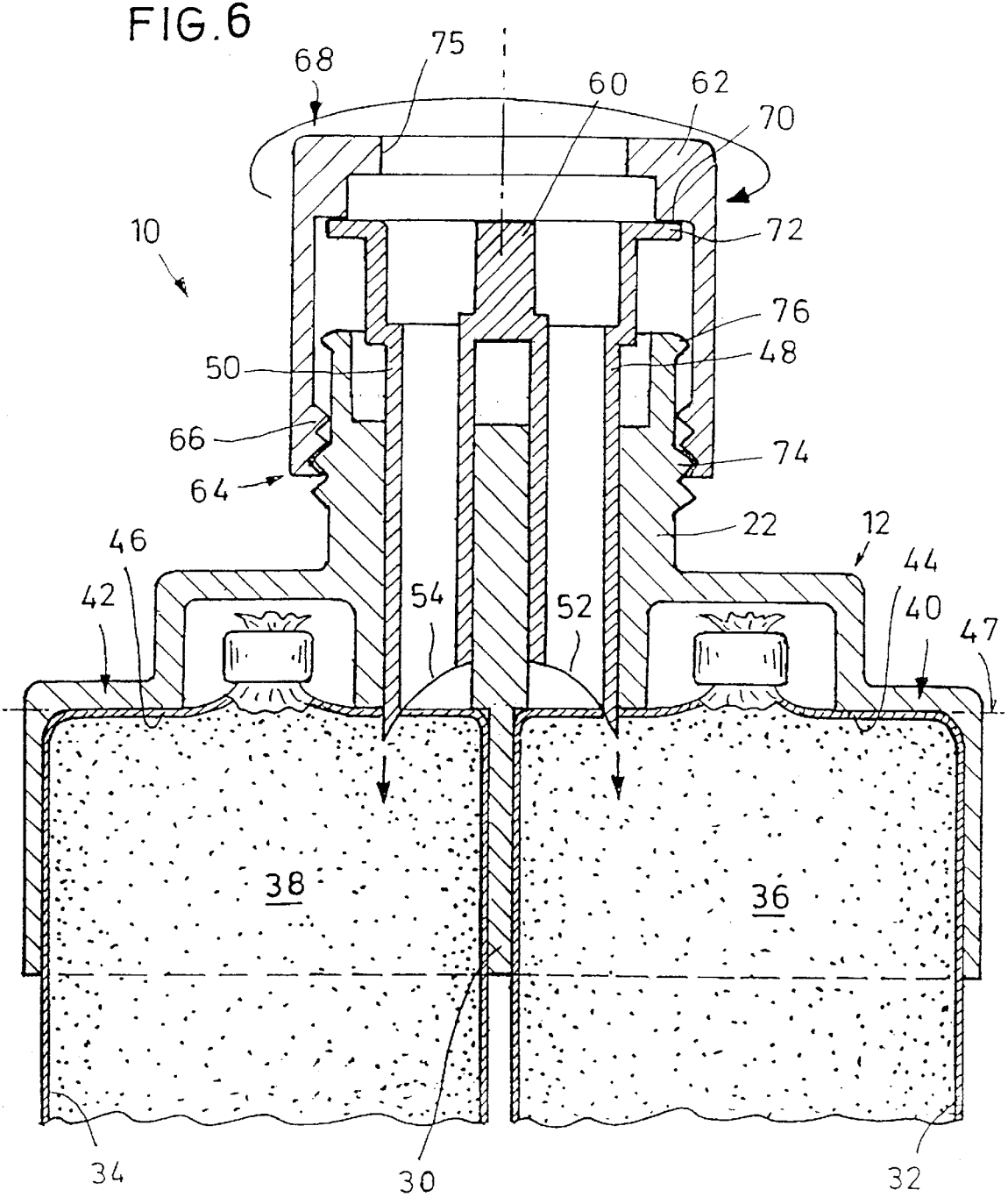

FIG. 1 is a partially sectional lateral view of a discharge device 110 for pasty two-component mixtures. The discharge device 110 comprises a rigid supply container 112 including two substantially cylindrical chambers 114 arranged to receive respectively one pasty component. On the front end 116, the supply container 112 comprises an end wall 118 with two outlet stubs 120 projecting therefrom, each of them corresponding to one of the chambers 114.

Arranged around the outlet stubs 120 is a receiving collar or a holding shell 122 arranged for rotation on the end wall 118 of supply container 112. On its front end 124 projecting beyond outlet stub 120 and facing away from end wall 118, the holding shell 122 is formed with a recess 126 provided as an opening surrounded on all sides by a recess edge 128.

Into the holding shell 122, there is inserted the coupling end 130 of a mixer unit 132 comprising a mixer housing 134 with a tubular portion 136. The tubular portion 136 has a mixer element 138 arranged therein. Tubular portion 136 has an outlet end 140 while the coupling end 130 comprises two inlet stubs 142 with separate channels 144 extending therefrom to mixer element 138.

As particularly evident from the plan view according to FIG. 2, the opening 1276 is of a substantially oval shape. The coupling end 130 of mixer housing 134 is shaped corresponding to this opening shape. Thus, with the holding shell 122 oriented according to FIG. 2, the mixer unit 132 can be moved by its coupling end 130 through the opening 126 until the inlet stubs 142 have been received by the outlet stubs 120. By subsequent rotation, the opening edge 128 of holding shell 122 is caused to grip over the two diametrically opposite and radially extending shoulder faces 146 in the transition region between the tubular portion 134 and the flange-like coupling end 130 of mixer unit 132. This locking position is shown in FIGS. 3 and 4. In this turned position of holding shell 122, the latter will thus have its opening edge 128 engage over the coupling end 130 of mixer unit 132 and will in this manner hold the mixer unit 132 in the operating state connected to supply container 112.

In the presently described discharge device, only the mixer unit 132 without the holding shell 122 has to be designed as a disposable article. This reduces the volume of disposable material for the mixer unit 132, which has a favourable effect on the environmental friendliness and, besides, on the production costs.

From FIGS. 2 and 4, it is further evident that the holding shell 122 in its two rotational end positions which in this embodiment are displaced by 90° relative to each other, is secured against respectively a further rotation. This is realized by a radially extending stopper element 148 on the holding shell 122, designed to abut against a respective counterpart element 150 arranged on end wall 118. The two counterpart elements 150 are arranged diametrically opposite each other and engage over an annular flange 152 of holding shell 122 so that, in addition to their function as rotation limiting elements, they provide for a rotatable support of holding shell 122 on supply container 112.

By lending a suitable shape to the opening 126 of holding shell 122, it is possible to encode the interface between mixer unit 132 and supply container 112 so that mixer unit 132 can be mounted only in case of a specific orientation of mixer unit 132 and holding shell 122. This coding can also be realized by additional engaging projection and recess elements on mixer unit 132 and supply container 112. For instance, the outlet stubs 120 and thus also the inlet stubs 142 can have different diameters or shapes.

The mixer interface has been described above as used in connection with a rigid supply container with a static mixer but is useful also for dynamic mixers provided with a rotatably driven mixer shaft. Further, the coupling of the mixer can be used also in a pressure container for pasty material accommodated in tube bags. Systems of this type require special opening mechanisms for opening the tube bags. Such a tube bag opening system will be described hereunder.

FIGS. 5 to 7 illustrate a first embodiment of a device 10 for opening two tube bags. The device 10 comprises a receiving cap 12 provided with an end wall 14 and an edge 16 projecting therefrom. Formed in the end wall 14 are two openings 18,20 in whose region a stub 22 projects from end wall 14 in a direction opposite to edge 16. The stub 22 is formed with two channels 24,26 starting from the openings 18,20 and extending to the discharge end 28 of stub 22 facing away from end wall 14. Between the two openings 18,20, end wall 14 comprises a partition wall 30 projecting from end wall 14 in the direction of edge 16. In this manner, two receiving chambers for two tube bags 32,34 are provided, each of them containing a pasty mass 36,38. The end sides 40,42 of the two tube bags 32,34 are surrounded by the receiving cap 12, or the edge 16 and the partition wall 30, with the end faces 44,46 of the tube bags 32,34 abutting the end wall 14 of the receiving cap along an abutment plane 47. The tube bags 32,34 can be connected to receiving cap 12, which is performed e.g. by bonding.

Each channel 24,26 has a piercing tube 48,50 arranged therein which has a bevelled and thus pointed piercing tube end 52,54. The two piercing tube tubes 48,50 are arranged for axial displacement in the channels 24,26 and in their retracted position according to FIG. 5 project beyond the discharge end 28 of stub 22. On their ends 56,58 facing away from the piercing tube ends 52,54, the two piercing tube tubes 48,50 are connected to each other as illustrated at 60. First, the piercing tube tubes 48,50 are provided to open the tube bags 32,34 by penetrating into the end faces 44,46, and, second, they shall allow the pasty substances 36,38 to pass for discharging them in the opened state of the tube bags 32,34.

Arranged in stub 22 is a screw cap 62 serving as an operating element for axial displacement of the piercing tube tubes 48,50. The screw cap 62 is substantially cylindrical and is provided, on one end 64 facing towards the receiving cap 12, with an inner thread portion 66. On the other end 66, the screw cap 62 is provided with an inner shoulder 70 abutting a surrounding radial flange of the two piercing tube tubes 48,50. Between the inner shoulder 70 and the inner thread portion 66, the screw cap 62 is formed smooth and without projections on its inner side.

In the central region along its radial extension, stub 22 comprises an outer thread portion 74 adapted to be brought into threaded engagement with the inner thread portion 66 of screw cap 62. Above and below the outer thread portion 74 of stub 22, the latter comprises smooth, projection-free regions of a similar or slightly larger axial extension as compared to the axial extension of the inner thread portion 66. At its front end 28 facing away from receiving cap 12, stub 22 is provided with an external securement projection 76.

In the production process, the screw cap 62 is shifted via the securement projection 76 onto the stub 22 until the inner thread portion 66 is located between the securement projection 76 and the outer thread portion 74 of stub 22 (see FIG. 5). In this situation, the piercing tubes 48,50, which have been inserted into the channels 24,26 before the screw cap 62, are arranged in their retracted position in which their piercing tube tips 52,54 do not project beyond the abutment plane 47. The piercing tube mandrels 52,54 will remain in this retracted position also when the screw cap 62 is subjected to a force in the axial direction since the inner thread and outer thread portions 66,74 prevent movement of cap 62. Only when rotating the screw cap 62 while simultaneously applying slight axial pressure, the screw cap 62 is moved in the axial direction since the two thread portions 66,74 are brought into or are in threaded engagement (see FIG. 6). By this axial movement of screw cap 62, also the piercing mandrels 48,50 are axially advanced so that their piercing tips 52,54 will pierce into the end faces 44,46 of the tube bags 32,34. The piercing mandrels 48,50 are completely in their advanced position in which their piercing tips 52,54 extend beyond the abutment plane 47 when the two thread portions 66,74 have again been brought out of their mutual engagement by further rotation of the screw cap 62 (see FIG. 7). In this situation, an axial displacement of the screw cap 62 is in turn prevented by the mutually blocking thread portions 66,74 so that the piercing mandrels 48,50 are secured in their advanced position.

Now, as indicated in FIG. 7, it is possible to connect to the piercing mandrel 48,50 a dynamic or static mixer 77 for mixing the pasty material 36,38 passing through the piercing mandrels 48,50. The mixer 77 is held on the screw cap 62, notably in the same manner in which the mixer unit 132 is held by means of the holding shell 122 to the supply container 112 according to FIGS. 1 to 4. Thus, the screw cap 62 fulfils a dual function, in that, starting from FIG. 6, it is first used for the advancing of the piercing mandrels 48,50 into the tube bags 32,34 (FIGS. 7 and 8) and then, by corresponding rotational positioning, will bring about the "correct orientation" of its opening 75 relative to the coupling end 73 of mixer 77 so that this coupling end 73 can be inserted into the screw cap 62 from above. Subsequently, the screw cap 62 is rotated to allow for the fixation of the mixer 77 in the manner of a bayonet lock as indicated in greater detail in FIGS. 1 to 4. These rotational movements of the screw cap 62 are performed in the position according to FIG. 7 in which the screw cap 62 is free of the threaded engagement with the stub 22.

The arresting of the screw cap 62 in its receiving rotational position and the locking rotational position, and the limiting of its rotation, as described in connection with the holding shell 122 according to the embodiment of FIGS. 1 to 4, can be realized by locking the screw cap 62 to the receiving cap 12. Since the axial distance of the screw cap 62 from the receiving cap 12 when screwing the latter onto stub 22 for advancing the piercing mandrels 48,50, is different from the position according to FIG. 7, the locking and the limiting of movement can be provided by such a design that locking projections and recesses required for this purpose as well as stoppers will cooperate only when the thread portions 66,74 according to FIG. 7 are out of engagement.

FIGS. 8 and 9 show an alternative embodiment of the opening device 10'. In as far as the individual parts of this device 10' correspond to those according to FIGS. 5 to 6 or are identical in function, such parts are provided with identical reference numerals with prime symbols. In the device 10', a separate receiving cap 12' with an end wall 14' and a surrounding projecting edge 16' is provided for each tube bag 32',34'. Each receiving cap 12' comprises a stub 22' formed with a channel 24' or 26' extending therethrough. These two channels 24',26' in turn have to piercing tubes 48',50' arranged therein which in the retracted position according to FIG. 8 project beyond the ends 28' of the stubs 22'. The piercing tubes 48',50' are connected to each other at 60' on their ends 56',58' facing away from receiving cap 12'. For securing the piercing tubes 48',50' against undesired movements from their retracted positions according to FIG. 8, the device 10' comprises a protective cap 78 which is detachably connected to stub 22'; in FIG. 8, this condition is realized by corresponding grip-over and grip-under projections 80,82 on the stub 22' and the cap 78, respectively. By rotating the cap 78, these projections 80,82 can be released from their mutual engagement so that the cap 78 can be removed. By manual pressure on the ends 56',58' and respectively the connection 60' of the two piercing tubes 48',50', the latter can be axially moved in the channels 24',26' beyond the abutment plane 47' and into the tube bags 32',34' (see FIG. 9). Subsequently, the mixer is mounted onto the piercing tubes 48',50' while the mixer is secured on the stubs 22' by corresponding securement elements.

Figure 10:
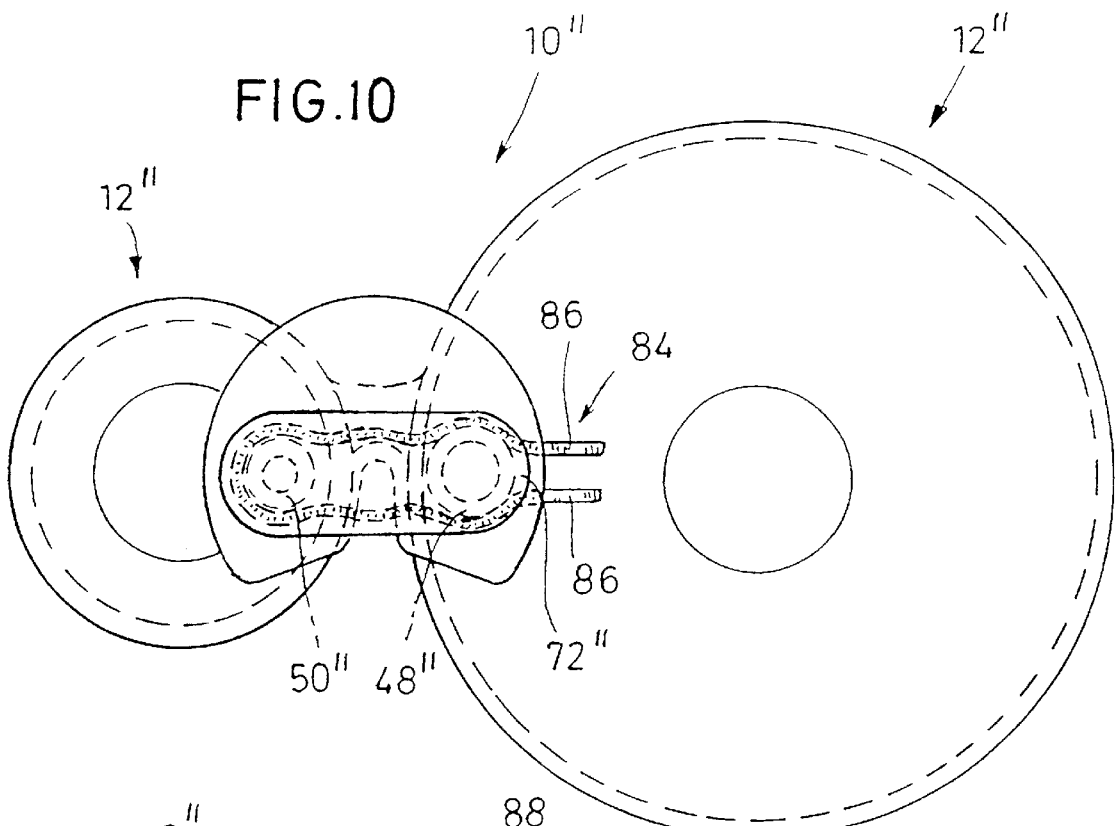
FIGS. 10 and 11 are views of an alternative embodiment of the device according to FIGS. 8 and 9.
Figure 11:
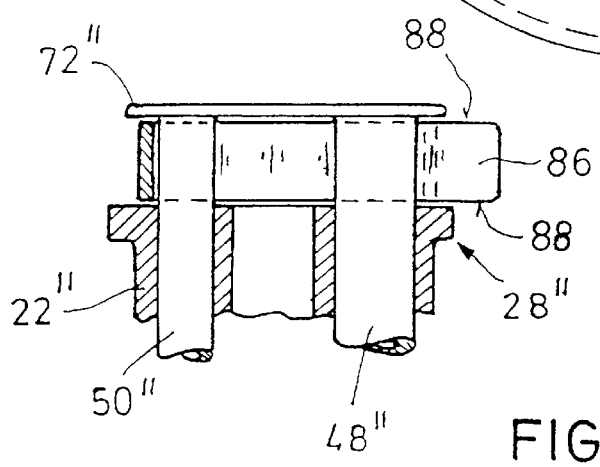

FIGS. 10 and 11 show a third embodiment of a device 10" which is designed as an alternative to the device 10'. The difference to the device 10' resides in the securement of the piercing tubes 48',50' against undesired movements from the retracted position into the advanced position. In the variant according to FIGS. 10 and 11, use is made of a spacer 84 formed as a resilient clip, externally surrounding the piercing tubes 48',50' projecting from the ends 28" of the stubs 22" and thus being arranged between the surrounding outer flange 72" of the piercing tubes 48",50" and the end 28" of the stubs 22" (see FIG. 11). The clip 84 is formed as a two-legged bracket whose two legs 86 have their mutually opposite longitudinal edges 88 abut on the flange 72" on the one hand and on the ends 28" of the stubs 22" on the other hand. By lateral withdrawal of the clip 84, the piercing tubes 48",50" are released and thus can be axially advanced by pressing them down.

Although a preferred embodiment of the invention has been specifically illustrated and described herein, it is to be understood that minor variations may be made in the apparatus without departing from the spirit and scope of the invention, as defined the appended claims.

What is claimed is:

1. A device for the discharge of a pasty two-component mixture comprising:

a supply container (112) with two chambers (114) for respectively one pasty component of the mixture, the supply container (112) being provided with a respective outlet stub (120) for each chamber (114), a mixer unit (132) comprising a tubular mixer housing (134) with a mixer element (138) arranged therein, the mixer housing (134) comprising a coupling end (130) to be coupled to the supply container (112) and having a two inlet stubs (142) and two channels (144) for the pasty components of the mixture leading to the mixer element (136), and comprising, on its opposite end, an outlet opening (140) for the mixture, the inlet stubs (142) being adapted for insertion into the outlet stubs (120) or vice versa, and a holding shell (122) for the coupling end (130) of the mixer housing (134) arranged for rotation on the supply container, the holding shell (122) surrounding the two outlet stubs (120) and comprising a recess (126) of a shape at least in parts substantially identical with the cross sectional shape of the coupling end (130) of the mixer housing (134), the holding shell (122) being rotatable between a receiving rotational position in which the recess (126) is oriented corresponding to the orientation of the coupling end (130) of the mixer housing (134) in the state where the inlet stubs (142) are connected to the outlet stubs (120) of the supply container (122), and a locking rotational position in which at least a part of the recess edge (128) of the holding shell (122) is in engagement over parts of the coupling end (130) of the mixer housing (134).

2. The device according to claim 1, characterized in that the coupling end (130) of the mixer housing (134) has a substantially oval cross-sectional shape and comprises two diametrically opposite flange portions (146) radially projecting beyond the tubular portion of the mixer housing (134) and provided for engagement from above through the recess edge (128) of the holding shell (122) in the locking rotational position of the recess edge.

3. The device according to claim 1, characterized in that the supply container (112) and the holding shell (122) are provided with cooperating stopper elements (148,150) for limiting the rotational movement of the holding shell (122) between the receiving and the locking rotational positions thereof.

4. The device according to claim 2, characterized in that the supply container (112) and the holding shell (122) are provided with cooperating stopper elements (148,150) for limiting the rotational movement of the holding shell (122) between the receiving and the locking rotational positions thereof.

5. The device according to claim 1, characterized in that the supply container (112) and the holding shell (122) have arranged thereon devices for preventing unintended advance and/or reverse rotation of the holding shell (122) in the receiving and the locking rotational positions thereof.

6. The device according to claim 2, characterized in that the supply container (112) and the holding shell (122) have arranged thereon devices for preventing unintended advance and/or reverse rotation of the holding shell (122) in the receiving and the locking rotational positions thereof.

7. The device according to claim 3, characterized in that the supply container (112) and the holding shell (122) have arranged thereon devices for preventing unintended advance and/or reverse rotation of the holding shell (122) in the receiving and the locking rotational positions thereof.

8. The device according to claim 1, characterized in that the supply container (12;122) comprises an end wall (118;14,14') formed with an abutment plane (47) for the end faces (44,46;44',46') of two tube bags (32,34;32',34') to be inserted into the chambers (114), that the two outlet stubs (120;22;22') have respectively an axially displaceable piercing tube (48,50;48',50') arranged therein, and that the piercing tubes (48,50;48',50') can be manually displaced from a retracted position in which the piercing tubes (48,50;48',50') do not extend beyond the abutment plane (47;47') into an advanced position in which in the piercing tubes (48,50;48', 50') extend beyond the abutment plane (47;47').

9. The device according to claim 2, characterized in that the supply container (12;122) comprises an end wall (118;14,14') formed with an abutment plane (47) for the end faces (44,46;44',46') of two tube bags (32,34;32',34') to be inserted into the chambers (114), that the two outlet stubs (120;22;22') have respectively an axially displaceable piercing tube (48,50;48',50') arranged therein, and that the piercing tubes (48,50;48',50') can be manually displaced from a retracted position in which the piercing tubes (48,50;48',50') do not extend beyond the abutment plane (47;47') into an advanced position in which in the piercing tubes (48,50;48', 50') extend beyond the abutment plane (47;47').

10. The device according to claim 3, characterized in that the supply container (12;122) comprises an end wall (118;14,14') formed with an abutment plane (47) for the end faces (44,46;44',46') of two tube bags (32,34;32',34') to be inserted into the chambers (114), that the two outlet stubs (120;22;22') have respectively an axially displaceable piercing tube (48,50;48',50') arranged therein, and that the piercing tubes (48,50;48',50') can be manually displaced from a retracted position in which the piercing tubes (48,50;48',50') do not extend beyond the abutment plane (47;47') into an advanced position in which in the piercing tubes (48,50;48', 50') extend beyond the abutment plane (47;47').

11. The device according to claim 5, characterized in that the supply container (12;122) comprises an end wall (118;14,14') formed with an abutment plane (47) for the end faces (44,46;44',46') of two tube bags (32,34;32',34') to be inserted into the chambers (114), that the two outlet stubs (120;22;22') have respectively an axially displaceable piercing tube (48,50;48',50') arranged therein, and that the piercing tubes (48,50;48',50') can be manually displaced from a retracted position in which the piercing tubes (48,50;48',50') do not extend beyond the abutment plane (47;47') into an advanced position in which in the piercing tubes (48,50;48', 50') extend beyond the abutment plane (47;47').

12. The device according to claim 8, characterized in that the piercing tubes (48,50;48',50') in their advanced positions are arranged in the stubs (120;22;22') while secured against undesired return movement in the direction of the retracted positions.

13. The device according to claim 8, characterized in that the piercing tubes (48,50;48',50') in their retracted positions project beyond the discharge end (28,28') of the stubs (120;22;22') facing away from the end wall (118;14;14').

14. The device according to claim 12, characterized in that the piercing tubes (48,50;48',50') in their retracted positions project beyond the discharge end (28,28') of the stubs (120;22;22') facing away from the end wall (118;14;14').

15. The device according to claim 8, characterized in that the piercing tubes (48,50;48',50') in their retracted positions are arranged in the stubs (22;22') while secured against undesired movements in the direction of the advanced positions.

16. The device according to claim 12, characterized in that the piercing tubes (48,50;48',50') in their retracted positions are arranged in the stubs (22;22') while secured against undesired movements in the direction of the advanced positions.

17. The device according to claim 13, characterized in that the piercing tubes (48,50;48',50') in their retracted positions are arranged in the stubs (22;22') while secured against undesired movements in the direction of the advanced positions.

18. The device according to claim 13, characterized in that a removable protective cap (78) can be pushed over the discharge end (28') of the stubs (22') and be fixed to the stubs (22').

19. The device according to claim 15, characterized in that a removable protective cap (78) can be pushed over the discharge end (28') of the stubs (22') and be fixed to the stubs (22').

20. The device according to claim 13, characterized in that the piercing tubes (48",50"), on their ends facing away from the supply container (112), are provided with an outer projection (72"), and that a removable spacer (84) can be positioned between the outer projections (72") and the discharge ends (281") of the stubs (22").

21. The device according to claim 15, characterized in that the piercing tubes (48",50"), on their ends facing away from the supply container (112), are provided with an outer projection (72"), and that a removable spacer (84) can be positioned between the outer projections (72") and the discharge ends (28") of the stubs (22").

22. The device according to claim 8, characterized in that an axially displaceable operating element (62) is arranged externally around the stubs (22) for moving the piercing tubes (48,50) from the retracted positions into the advanced positions, the operating element (62) comprising an abutment face (70) for abutment on the piercing tubes (48,50).

23. The device according to claim 12, characterized in that an axially displaceable operating element (62) is arranged externally around the stubs (22) for moving the piercing tubes (48,50) from the retracted positions into the advanced positions, the operating element (62) comprising an abutment face (70) for abutment on the piercing tubes (48,50).

24. The device according to claim 13, characterized in that an axially displaceable operating element (62) is arranged externally around the stubs (22) for moving the piercing tubes (48,50) from the retracted positions into the advanced positions, the operating element (62) comprising an abutment face (70) for abutment on the piercing tubes (48,50).

25. The device according to claim 15, characterized in that an axially displaceable operating element (62) is arranged externally around the stubs (22) for moving the piercing tubes (48,50) from the retracted positions into the advanced positions, the operating element (62) comprising an abutment face (70) for abutment on the piercing tubes (48,50).

26. The device according to claim 18, characterized in that an axially displaceable operating element (62) is arranged externally around the stubs (22) for moving the piercing tubes (48,50) from the retracted positions into the advanced positions, the operating element (62) comprising an abutment face (70) for abutment on the piercing tubes (48,50).

27. The device according to claim 20, characterized in that an axially displaceable operating element (62) is arranged externally around the stubs (22) for moving the piercing tubes (48,50) from the retracted positions into the advanced positions, the operating element (62) comprising an abutment face (70) for abutment on the piercing tubes (48,50).

28. The device according to claim 22, characterized in that the operating element (62) can be locked, in two movement positions, to the stub (22) and/or to the supply container (12) for preventing undesired axial movements.

29. The device according to claim 28, characterized in that the operating element (62) comprises an inner thread portion (66) and the stubs (22) comprise an outer thread portion (74) adapted for threaded engagement with the inner thread portion (66), that the outer thread portion (74) is spaced from the end wall of the supply container (12) as well as from the discharge ends (28) of the stubs (22) by at least the axial extension of the inner thread portion (66) of the operating element (62), and that the inner thread portion (66) of the operating element (62) is arranged, while spaced from the abutment face (70) of the operating element (62) by at least the axial extension of the outer thread portion (74) of the stubs (22), on the end (64) of the operating element (62) facing towards the supply container (12).

30. The device according to claim 28, characterized in that the operating element (62) is the holding shell (122) for holding the mixer unit (77).

31. The device according to claim 29, characterized in that the operating element (62) is the holding shell (122) for holding the mixer unit (77).

32. A device for opening a tube bag containing a pasty substance, comprising
a receiving cap (14;14';14") for receiving an end side (40;42;40';42') of the tube bag (32;34;32';34'), which end side comprises an end face (44;46;44';46'), the receiving cap (14;14';14") comprising an end wall (14;14') forming an abutment plane (47;47') for the end face (44;46;44';46') of the tube bag (32;34;32';34'), and an edge (16;16') extending from the end wall,
an opening (18;20;18';20') formed in the end wall (14;14') and surrounded by a stub (22;22') projecting from the end wall (14;14'), and
a piercing tube (48;50;48';50') guided in the stub (22;22') for axial displacement, characterized in that the piercing tube (48;50;48';50') is manually displaceable from a retracted position in which the piercing tube (48;50;48';50') does not extend beyond the abutment plane (47;47') into an advanced position in which in the piercing tube (48;50;48';50') extends beyond the abutment plane (47;47').

33. The device according to claim 32, characterized in that the piercing tube (48,50;48',50') in its advanced position is arranged in the stub (22; 22') while secured against undesired return movement in the direction of the retracted position.

34. The device according to claim 32, characterized in that the piercing tube (48,50;48',50') in its retracted position projects beyond the discharge end (28,28') of the stub (22;22') facing away from the end wall (14; 14').

35. The device according to claim 33, characterized in that the piercing tube (48,50;48',50') in its retracted position projects beyond the discharge end (28,28') of the stub (22;22') facing away from the end wall (14;14').

36. The device according to claim 32, characterized in that the piercing tube (48,50;48',50') in its retracted position is arranged in the stub (22;22') while secured against undesired movements in the direction of the advanced position.

37. The device according to claim 33, characterized in that the piercing tube (48,50;48',50') in its retracted position is arranged in the stub (22;22') while secured against undesired movements in the direction of the advanced position.

38. The device according to claim 34, characterized in that the piercing tube (48,50;48',50') in its retracted position is arranged in the stub (22;22') while secured against undesired movements in the direction of the advanced position.

39. The device according to claim 34, characterized in that a removable protective cap (78) can be pushed over the discharge end (28') of the stub (22') and be fixed to the stub (22').

40. The device according to claim 36, characterized in that a removable protective cap (78) can be pushed over the discharge end (28') of the stub (22') and be fixed to the stub (22').

41. The device according to claim 34, characterized in that the piercing tube (48",50"), on its end facing away from the end wall of the receiving cap (12"), is provided with an outer projection (72"), and that a removable spacer (84) can be positioned between the outer projection (72") and the discharge end (28") of the stub (22").

42. The device according to claim 36, characterized in that the piercing tube (48",50"), on its end facing away from the end wall of the receiving cap (12"), is provided with an outer projection (72"), and that a removable spacer (84) can be positioned between the outer projection (72") and the discharge end (28") of the stub (22").

43. The device according to claim 32, characterized in that an axially displaceable operating element (62) is arranged externally around the stub (22) for moving the piercing tube (48,50) from the retracted position into the advanced position, the operating element (62) comprising an abutment face (70) for abutment on the piercing tube (48,50).

44. The device according to claim 33, characterized in that an axially displaceable operating element (62) is arranged externally around the stub (22) for moving the piercing tube (48,50) from the retracted position into the advanced position, the operating element (62) comprising an abutment face (70) for abutment on the piercing tube (48,50).

45. The device according to claim 34, characterized in that an axially displaceable operating element (62) is arranged externally around the,stub (22) for moving the piercing tube (48,50) from the retracted position into the advanced position, the operating element (62) comprising an abutment face (70) for abutment on the piercing tube (48,50).

46. The device according to claim 36, characterized in that an axially displaceable operating element (62) is arranged externally around the stub (22) for moving the piercing tube (48,50) from the retracted position into the advanced position, the operating element (62) comprising an abutment face (70) for abutment on the piercing tube (48,50).

47. The device according to claim 39, characterized in that an axially displaceable operating element (62) is arranged externally around the stub (22) for moving the piercing tube (48,50) from the retracted position into the advanced position, the operating element (62) comprising an abutment face (70) for abutment on the piercing tube (48,50).

48. The device according to claim 41, characterized in that an axially displaceable operating element (62) is arranged externally around the stub (22) for moving the piercing tube (48,50) from the retracted position into the advanced position, the operating element (62) comprising an abutment face (70) for abutment on the piercing tube (48,50).

49. The device according to claim 43, characterized in that the operating element (62) can be locked, in two movement positions, to the stub (22) and/or to the supply container (12) for preventing undesired axial movements.

50. The device according to claim 49, characterized in that the operating element (62) comprises an inner thread portion (66) and the stub (22) comprises an outer thread portion (74) adapted for threaded engagement with the inner thread portion (66), that the outer thread portion (74) is spaced from the receiving cap (12) as well as from the discharge end (28) of the stub (22) by at least the axial extension of the inner thread portion (66) of the operating element (62), and that the inner thread portion (66) of the operating element (62) is arranged, while spaced from the abutment face (70) of the operating element (62) by at least the axial extension of the outer thread portion (74) of the stub (22), on the end (64) of the operating element (62) facing towards the receiving cap (12).

51. The device according to claim 32, characterized in that two piercing tubes (48,50) are guided for axial displacement in the receiving stub (22).

52. The device according to claim 33, characterized in that two piercing tubes (48,50) are guided for axial displacement in the receiving stub (22).

53. The device according to claim 34, characterized in that two piercing tubes (48,50) are guided for axial displacement in the receiving stub (22).

54. The device according to claim 36, characterized in that two piercing tubes (48,50) are guided for axial displacement in the receiving stub (22).

55. The device according to claim 39, characterized in that two piercing tubes (48,50) are guided for axial displacement in the receiving stub (22).

56. The device according to claim 41, characterized in that two piercing tubes (48,50) are guided for axial displacement in the receiving stub (22).

57. The device according to claim 43, characterized in that two piercing tubes (48,50) are guided for axial displacement in the receiving stub (22).

58. The device according to claim 49, characterized in that two piercing tubes (48,50) are guided for axial displacement in the receiving stub (22).

59. The device according to claim 50, characterized in that two piercing tubes (48,50) are guided for axial displacement in the receiving stub (22).

* * * * *